United States Patent [19]

Sauers

[11] 4,146,618

[45] Mar. 27, 1979

[54] SUBSTITUTED CARBAMATES

[75] Inventor: Richard F. Sauers, Hockessin, Del.

[73] Assignee: E. I. Du Pont de Nemours and Company, Wilmington, Del.

[21] Appl. No.: 867,120

[22] Filed: Jan. 5, 1978

[51] Int. Cl.$^2$ ............................ A01N 9/00; C07F 7/02
[52] U.S. Cl. ............................ 424/184; 260/448.2 E; 260/448.2 N
[58] Field of Search ................. 424/184; 260/448.2 N

[56] References Cited

U.S. PATENT DOCUMENTS 3,576,834   4/1971   Buchanan .............................. 260/453

Primary Examiner—Allen J. Robinson

[57] ABSTRACT

Insecticidal carbamates, such as ethanimidothioic acid N-[((N-methyl-N-(trimethylsilanyl)amino]-carbonyloxy)]methyl ester, for control of pestiferous insects belonging to such orders as Lepidoptera, Coleoptera and Diptera.

12 Claims, No Drawings

SUBSTITUTED CARBAMATES

BACKGROUND OF THE INVENTION

This invention relates to insecticidal carbamates. U.S. Pat. No. 3,576,834, granted Apr. 27, 1971, covers insecticides such as methomyl:

$$CH_3-C(S-CH_3)=NO-C(=O)-NH-CH_3$$

German Pat. No. 2,208,329 (1972) discloses trialkylsilylamino-s-triazines as herbicides:

(structure of triazine with $R_1$ at top, $R_2NH$ and $NHSiR_3$ substituents)

wherein
  $R_1$ is cyano, azido, halo, alkoxy or alkylthio;
  $R_2$ is alkyl, alkenyl, alkinyl, cycloalkyl, alkoxyalkyl, cyanoalkyl, alkoxycycloalkyl or cyanocycloalkyl;
  $R_3$ is alkyl.

SUMMARY OF THE INVENTION

This invention relates to compounds of Formula I, to insecticidal compositions containing them and to the method of using these compounds as insecticides.

$$\underset{R_2S}{\overset{R_1}{>}}C=NOC(=O)N(R_3)-Si(R_4)(R_5)(R_6) \quad (I)$$

wherein
  $R_1$ is methyl or ethyl;
  $R_2$ is alkyl of one to three carbons, either branched or straight chain;
  $R_3$ is hydrogen or methyl;
  $R_4$ and $R_5$ are independently alkyl of one to four carbons, either branched or straight chain; and
  $R_6$ is alkyl of one to four carbons, either branched or straight chain, or phenyl.

DETAILED DESCRIPTION OF THE INVENTION

Preferred Compounds

Compounds which are preferred for their high insecticidal activity or favorable cost or both are those compounds of Formula I wherein
  $R_2$ is methyl; and
  $R_4$ and $R_5$ are independently methyl or ethyl; and
  $R_6$ is alkyl of one to four carbons, either branched or straight chain.

More preferred for their higher insecticidal activity or more favorable cost or both are said preferred compounds wherein $R_3$ is methyl.

Specifically preferred for its outstanding insecticidal activity or highly favorable cost or both is ethanimidothioic acid N-[((N-methyl-N-(trimethylsilanyl)-amino]-carbonyloxy)]methyl ester, having the formula:

$$CH_3C(SCH_3)=NOC(=O)N(CH_3)Si(CH_3)_3.$$

Preparation

The compounds of Formula I can be prepared, as shown in Equation A, by reacting at least one mole of a substituted N-(aminocarbonyloxy)-alkanimidothioic acid ester of Formula II with one mole of a trisubstituted halosilane of Formula III in the presence of base:

Equation A $$\underset{SR_2}{\overset{R_1}{>}}C=NOC(=O)N(R_3)-H + X-Si(R_4)(R_6)-R_5 \xrightarrow{\text{(base)}}$$

(II) \qquad (III)

$$\underset{SR_2}{\overset{R_1}{>}}C=NOC(=O)N(R_3)-Si(R_4)(R_6)-R_5 + HX.$$

(I)

wherein each of $R_1$–$R_6$ is as previously defined and X is halogen.

The reaction can be carried out in any inert organic solvent, e.g. methylene chloride, dioxane, tetrahydrofuran chloroform, 1,2-dichlorethane, acetonitrile, benzene, toluene, the xylenes, etc. Mixtures of these solvents can also be used.

Any organic or inorganic base which can function as an acid acceptor can be used in synthesizing the compounds of this invention, e.g. pyridine, trialkylamines such as trimethylamine and triethylamine, N,N-dimethylaniline, the hydroxides, carbonates and bicarbonates of the alkali metals and alkaline earths, and the alkoxides of the alkali metals, such as sodium methoxide and potassium tert-butoxide.

The process can be carried out at a temperature of between about −20° and 60° C., preferably between about −5° and 40° C. Pressure is not critical, for convenient atmospheric pressure is preferred.

The starting materials, (II), can be prepared by techniques described in U.S. Pat. Nos. 3,574,736; 3,576,834 and 3,787,470.

In the compounds of Formula III, chlorides are the preferred halogen for economic reasons; however, bromides, iodides and fluorides may be used. Compounds of Formula III can be prepared by a suitable modification of the methods descrived in *Organosilicon Compounds*, C. Eaborn, Academic Press, Inc., New York, N.Y. (1960), pages 167–193.

Other routes for preparing compounds of this invention may be used, e.g.:

$$R_6-Si(R_4)(R_5)NCO + \underset{SR_2}{\overset{R_1}{>}}C=NOH \longrightarrow$$

$$\underset{SR_2}{\overset{R_1}{>}}C=NOC(=O)NHSi(R_4)(R_6)-R_5$$

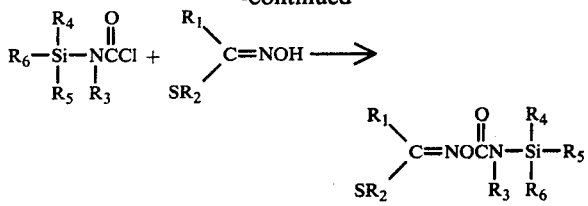

The compounds of Formula I are insoluble in water and generally soluble in most polar organic solvents such as acetone and dimethylformamide.

EXAMPLE 1

Ethanimidothioic acid N-[([n-methyl-N-(trimethylsilanyl)-amino]carbonyloxy)]methyl ester Under a slow nitrogen purge a solution of 48.6 parts of methomyl in 300 parts of THF was cooled to −5°. A solution of 40.5 parts of trimethyl chlorosilane in 50 parts of THF was quickly added to the solution above. Then a solution of 38.4 parts of triethyl amine in 50 parts of THF was added dropwise at −5° to +5° over a 30-minute period. The reaction mixture was allowed to warm to room temperature gradually, then stirred overnight under nitrogen.

The precipitate was filtered off and the filtrate stripped to a viscous oil. The oil was dissolved in 1-chlorobutane and seeded with methomyl. About 8 parts of unreacted methomyl was filtered off and the filtrate stripped to a viscous oil which slowly crystallized. Recrystallization from cyclohexane gave 48.7 parts of ethanimidothioic acid N-[([N-methyl-N-(trimethylsilanyl)amino]carbonyloxy)]methyl ester as a pale pink solid, m.p. 47°–57°. Recrystallization from ethanol-water gave a white solid, m.p. 58°–60°.

IR (Nijol)$\gamma_{MAX}$ 1740 (C═O), 1595 (C═N).

NRM (CDCl$_3$) δ0.3 (S, Me$_3$Si); 2.4 (S, MeS); 2.55 (S, MeC═N). 3.0 (S, MeN). Anal. Calcd. for C$_8$H$_{18}$N$_2$O$_2$SSi: C, 40.99; H, 7.74; N, 11.95; S, 13.68. Found: C. 40.49, 40.30; H, 7.39, 7.11; N, 12.19, 12.29; S, 13.83.

By reacting equivalent amounts of other compounds of Formula (II) with compounds of Formula III using the procedure of Example 1, the following compounds of Formula I set forth in Table I can be prepared.

TABLE I

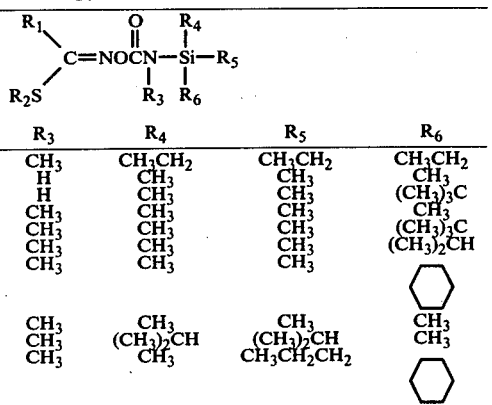

| R$_1$ | R$_2$ | R$_3$ | R$_4$ | R$_5$ | R$_6$ |
|---|---|---|---|---|---|
| CH$_3$ | CH$_3$ | CH$_3$ | CH$_2$CH$_2$ | CH$_2$CH$_2$ | CH$_2$CH$_2$ |
| CH$_3$ | CH$_3$ | H | CH$_3$ | CH$_3$ | CH$_3$ |
| CH$_3$ | CH$_3$ | H | CH$_3$ | CH$_3$ | (CH$_3$)$_3$C |
| CH$_2$CH$_2$ | CH$_3$ | CH$_3$ | CH$_3$ | CH$_3$ | CH$_3$ |
| CH$_3$ | CH$_3$ | CH$_3$ | CH$_3$ | CH$_3$ | (CH$_3$)$_3$C |
| CH$_3$ | CH$_3$ | CH$_3$ | CH$_3$ | CH$_3$ | (CH$_3$)$_2$CH |
| CH$_3$ | CH$_3$ | CH$_3$ | CH$_3$ | CH$_3$ | ⬡ |
| CH$_3$ | (CH$_3$)$_2$CH | CH$_3$ | CH$_3$ | CH$_3$ | CH$_3$ |
| CH$_3$ | CH$_3$ | CH$_3$ | (CH$_3$)$_2$CH | (CH$_3$)$_2$CH | CH$_3$ |
| CH$_3$ | CH$_3$ | CH$_3$ | CH$_3$ | CH$_3$CH$_2$CH$_2$ | ⬡ |

Formulation

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of a) about 0.1% to 20% surfactant(s) and b) about 1% to 99% solid or liquid diluent(s). More specifically, they will contain these ingredients in the approximate proportions set forth in Table II.

TABLE II

| | Percent by weight | | |
|---|---|---|---|
| | Active Ingredient | Diluent(s) | Surfactant(s) |
| Wettable Powders | 20–90 | 0–74 | 1–10 |
| Oil Suspensions Emulsions, Solutions, (including Emulsifiable Concentrates) | 5–50 | 40–95 | 0–15 |
| Aqueous Suspensions | 10–50 | 40–84 | 1–20 |
| Dust | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd Edn., Dorland Books, Caldwell, N.J. The more absorptive diluents are preferred for wettable powders and the denser ones for dusts. Typical liquid diluents and solvents are described in Marsden, "Solvents Guide", 2nd Edn., Interscience, New York, 1950. Solubility under 0.1% is preferred for suspension concentrates; solution concentrates are preferably stable against phase separation at 0° C. "McCutcheon Division, MC Publishing Co., Ridgewood, New Jersey, as well as Sisely and Wood, "Enclyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques.

See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8–59ff.

For further infromation regarding the art of formulation, see for example:

J. B. Buchanan, U.S. Pat. No. 3,576,834 Apr. 27, 1971, Col. 5, line 36 through Col. 7, line 70 and Exs. 1–4, 17, 106, 123–140.

R. R. Shaffer, U.S. Pat. No. 3,560,616 Feb. 2, 1971, Col. 3, line 48 through Col. 7, line 26 and Exs. 3–9, 11–18.

E. Somers, "Formulation", Chapter 6 in Torgeson, "Fungicides", Vol. I, Academic Press, New York, 1967.

EXAMPLE 2

| Granule | |
|---|---|
| Ethanimidothioic acid N-[([N-methyl-N-(trimethylsilanyl)amino]-carbonyloxy)]methyl ester | 10% |
| Attapulgite granules (low volative matter, 0.71/0.30 mm; U.S.S.# 25–50 sieves) | 90% |

The active ingredient is warmed to approximately 90° C. and sprayed upon dedusted and pre-warmed attapulgiate granules in a double cone blender. The granules are then allowed to cool and are packaged.

EXAMPLE 3

| Emulsifiable Concentrate | |
|---|---|
| Ethanimidothioic acid N-[([N-methyl-N-(trimethylsilanyl)amino]-carbonyloxy)]methyl ester | 30% |
| Blend of oil soluble sulfonates and polyoxyethylene ester | 4% |
| xylene | 66% |

The ingredients are combined and stirred with gentle warming to speed solution. A fine screen filter is included in the packaging operation to insure the absence of any extraneous undissolved material in the product.

EXAMPLE 4

| Wettable Powder | |
|---|---|
| Ethanimidothioic acid N-[([N-methyl-N-(trimethylsilanyl)amino]-carbonyloxy)]methyl ester | 40% |
| Dioctyl sodium sulfosuccinate | 1.5% |
| Sodium ligninsulfonate | 3% |
| Low viscosity methyl cellulose | 1.5% |
| Attapulgite | 54% |

The ingredients are thoroughly blended, passed through an air mill, to produce an average particle size under 15 microns, reblended, and sifted through a U.S. Ser. No. 50 sieve (0.3 mm opening) before packaging.

All compounds of the invention may be formulated in the same manner.

BIOLOGICAL DISCLOSURE AND EXAMPLES

The compounds of this invention are useful for control of insects which are detrimental to agriculture and public health. They readily control pestiferous insects belonging to such orders as Lepidoptera, Coleoptera and Diptera. More specifically, insects controlled by the compounds of this invention include but are not limited to: Mosquitoes (*Aedes aegypti*), southern armyworm (*Spodoptera eridania*), beet armyworm (*Spodoptera exigua*), soybean looper (*Pseudoplusia includens*), Mexican bean beetle (*Epilachna varivestis*), and Colorado potato beetle (*Leptinotarsa decemlineata*).

The insects are controlled by applying the material in a convenient formulation to the locus of infestation, to the area to be protected, or to the pests themselves. For the control of insects in agricultural crops, the compound is generally applied to the foliage or other plant parts which are infested or which are to be protected. Effective amounts to be applied depend upon the species to be controlled, its life stage, its size and location, the amount of rainfall, the time of year, moisture, temperature, type of application, and other variables. In general, 0.1 to 50 kg/ha may be required for insect control in agriculture with rates of 0.25 to 12.5 kg/ha usually being sufficient. Preferred rates in large-scale operations are in the range between 0.5 to 4 kg/ha. When used on an area-wide basis, as in the control of mosquito larvae, 0.05 to 25 kg/ha are generally sufficient and 0.1 to 1.25 kg/ha are preferred. Where penetration of the insect cuticle is needed for activity, addition of an adjuvant which acts as a penetrant may be beneficial.

The compounds of this invention will generally be used in formulation with a carrier that commonly will consist of oil or water. Applications may be made with concentrated or dilute solutions or suspensions of the insecticide in the carrier. Low-volume applications utilizing suspensions containing 18.75% of the active ingredient may be preferred by some applicators while others may prefer dilute solutions or suspensions containing only 62 ppm in high-volume applications.

Under some circumstances it may be desirable to add adjuvants such as activated charcoal or Panther Creek Clay to the formulations to improve crop safety. Whether such adjuvants are used will depend on the sensitivity of the crop, the quantity of active ingredients used, weather conditions and other factors.

The compound of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the compound of this invention may vary from 0.0625 to 25 parts by weight. Suitable agents of this type are well known to those skilled in the art. Some are listed below:

Fungicides:

methyl 2-benzimidazolecarbamate
tetramethyl thiuram disulfide (thiuram)
n-dodecylguanidine acetate (dodine)
manganese ehtylenebisdithiocarbamate (maneb)
1,4-dichloro-2,5-dimethoxybenzene (chloroneb)

methyl 1-(butylcarbamoyl)-2-benzimidazolecarbamate (benomyl)

N-trichloromethylthiotetrahydrophthalimide (captan)

N-trichloromethylthiophthalimide (folpet)

Bactericides:

tribasic copper sulfate
streptomycin sulfate

Acaricides:

senecioic acid, ester with 2-sec-butyl-4,6-dinitrophenol (Morocide ®)

6-methyl-1,3-dithiolo[2,3-B]quinonolin-2-one (Morestan ®)

ethyl 4,4'-dichlorobenzilate (Chlorobenzilate ®)

1,1-bis(p-chloropehnyl)-2,2,2-trichloroethane (Kelthane ®)

bis(pentachloro-2,4-cyclopentadien-lyl) (Pentac ®)

tricyclohexyl trihydroxide (Plictran ®)

Nematicides:

S-methyl 1-(dimethylcarbamoyl)-N-(methylcarbamoyloxy)-thioformimidate (Vydate ®)

S-methyl 1-carbamoyl-N-(methylcarbamoyloxy)thioformimidate

N-isopropylphosphoramidic acid, O-ethyl-O'-[4-(methylthio)-m-tolyl]diester (Nemacur ®)

Insecticides:

3-hydroxy-N-methylcrotonamide (dimethylphosphate)ester (Azodrin ®)

methylcarbamic acid, ester with 2,3-dihydro-2,2-dimethyl-7-benzofuranol (Furadan ®)

O-[2,4,5-trichloro-α-(chloromethyl)]benzylphosphoric acid, O', O'-dimethyl ester (Gardona ®)

2-mercaptosuccinic acid, diethyl ester, S-ester with thionophosphoric acid, dimethyl ester (Malathion ®)

phosphorothioic acid, O,O-dimethyl, O-p-nitrophenyl ester (methyl parathion)

methylcarbamic acid, ester with α-naphthol (carbaryl)

methyl O-(methylcarbamoyl)thiolacetohydroxamate (methomyl)

N'-(4-chloro-o-tolyl)-N,N-dimethylformamidine (Galecron ®)

O,O-diethyl-O-(2-isopropyl-4-methyl-6-pyrimidyl-phosphorothioate (Diazinon ®)

The following examples illustrate the insecticidal qualities of the compounds of this invention.

EXAMPLE 5

Red kidney bean plants in the two-leaf stage were sprayed to run-off with various concentrations of ethanimidothioic acid N-[([N-methyl-N-(trimethylsilanyl)-amino]-carbonyloxy)]methyl ester. Suspensions were made by dissolving 50 mg of the compound in 15 ml of acetone, adding 1 ml of 1% Methocel 15 solution and diluting to volume with a Duponol-water solution at 1:3000. After plants had dried, leaves were detached and placed singly in covered Petri dishes along with 10 southern armyworm larvae. Evaluations with respect to percent kill were made and are set forth below:

| Percent spray Concentration | Evaluation Percent Kill - 2 Days |
|---|---|
| .02 | 100 |
| .01 | 90 |
| .005 | 30 |
| Untreated Control | 0 |

EXAMPLE 6

The inside surfaces of 10 × 15 mm Petri dishes were coated uniformly with an acetone solution of ethanimidothioic aicd N-[([N-methyl-N-(trimethylsilanyl)amino]-carbonyloxy)]methyl ester. Shortly after the dishes were prepared, a group of 10 soybean looper larvae were placed in each. Evaluations with repsect to percent moribund and dead are listed below:

| | Evaluation Percent Moribund & Dead (Hrs.) | | | |
|---|---|---|---|---|
| μg/Dish | 2 | 4 | 7 | 23 |
| 4 | 100 | 100 | 100 | 100 |
| 2 | 80 | 80 | 80 | 90 |
| 1 | 40 | 60 | 60 | 90 |

What is claimed is:
1. A compound having the formula:

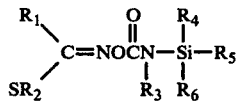

wherein
$R_1$ is methyl or ethyl;
$R_2$ is alkyl of one to three carbons, either branched or straight chain;
$R_3$ is hydrogen or methyl;
$R_4$ and $R_5$ are independently alkyl of one to four carbons, either branched or straight chain; and
$R_6$ is alkyl of one to four carbons, either branched or straight chain, or phenyl.

2. A compound of claim 1 wherein $R_2$ is methyl; and $R_4$ and $R_5$ are independently methyl or ethyl; and $R_6$ is alkyl of one to four carbons, either branched or straight chain.

3. A compound of claim 2 wherein $R_3$ is methyl.

4. A compound of claim 3 which is ethanimidothioic acid N-[([N-methyl-N-(trimethylsilanyl)-amino]carbonyloxy)]methyl ester, having the formula:

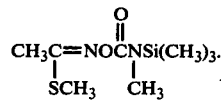

5. A composition suitable for control of pestiferous insects consisting essentially of an insecticidally effective amount of a compound of claim 1 and at least one of (a) an inert diluent and (b) a surfactant.

6. A composition suitable for control of pestiferous insects consisting essentially of an insecticidally effective amount of a compound of claim 2 and at least one of (a) an inert diluent and (b) a surfactant.

7. A composition suitable for control of pestiferous insects consisting essentially of an insecticidally effective amount of a compound of claim 3 and at least one of (a) an inert diluent and (b) a surfactant.

8. A composition suitable for control of pestiferous insects consisting essentially of an insecticidally effective amount of the compound of claim 4 and at least one of (a) an inert diluent and (b) a surfactant.

9. A method for control of pestiferous insects which comprises applying to a locus of infestation, to the area of the plant to be protected or to the pests themselves, an insecticidally effective amount of a compound of claim 1.

10. A method for control of pestiferous insects which comprises applying to a locus of infestation, to the area of the plant to be protected or to the pests themselves, an insecticidally effective amount of a compound of claim 2.

11. A method for control of pestiferous insects which comprises applying to a locus of infestation, to the area of the plant to be protected or to the pests themselves, an insecticidally effective amount of a compound of claim 3.

12. A method for control of pestiferous insects which comprises applying to a locus of infestation, to the area of the plant to be protected or to the pests themselves, an insecticidally effective amount of the compound of claim 4.

* * * * *